United States Patent [19]
Woodruff et al.

[11] Patent Number: 5,868,699
[45] Date of Patent: *Feb. 9, 1999

[54] INJECTION DART SYSTEM

[75] Inventors: Keith F. Woodruff, Mountainside, N.J.; David Alan Peterson, Pipersville; Kendra Beth Eager, Newtown, both of Pa.

[73] Assignee: American Cyanamid Company, Madison, N.J.

[ * ] Notice: The term of this patent shall not extend beyond the expiration date of Pat. No. 5,725,497.

[21] Appl. No.: 473,346

[22] Filed: Jun. 7, 1995

[51] Int. Cl.$^6$ .................................................. A61M 31/00
[52] U.S. Cl. ................................ 604/49; 604/51; 604/60; 604/93; 604/174; 604/264
[58] Field of Search ..................... 604/19, 49, 51, 604/56–57, 59–60, 93, 115–7, 130–1, 174–5, 177–8, 194, 231–2, 239, 264, 272–4, 282, 890.1, 891.1; 273/418–20, 422–3

[56] References Cited

U.S. PATENT DOCUMENTS

| | | |
|---|---|---|
| 1,651,499 | 12/1927 | Woodrow . |
| 1,819,415 | 8/1931 | Harris . |
| 2,620,190 | 12/1952 | Bean . |
| 3,277,893 | 10/1966 | Clark ........................................ 128/215 |
| 3,416,713 | 12/1968 | Stephens . |
| 3,893,866 | 7/1975 | Hollingsworth . |
| 3,948,263 | 4/1976 | Drake, Jr. et al. ...................... 128/260 |
| 4,103,893 | 8/1978 | Walker .................................... 604/130 |
| 4,147,164 | 4/1979 | Behney . |
| 4,174,837 | 11/1979 | Benke .................................... 273/418 |
| 4,214,585 | 7/1980 | Bailey, Jr. . |
| 4,243,036 | 1/1981 | Ott . |
| 4,490,139 | 12/1984 | Huizenga et al. . |
| 4,561,445 | 12/1985 | Berke et al. ............................ 604/274 |
| 4,671,789 | 6/1987 | Laby . |
| 4,713,053 | 12/1987 | Lee ....................................... 604/117 |
| 4,751,926 | 6/1988 | Sasaki . |
| 4,863,428 | 9/1989 | Chevalier . |
| 4,889,529 | 12/1989 | Haindl .................................... 604/274 |
| 4,905,397 | 3/1990 | Juelg, Jr. ................................ 273/416 |
| 5,034,229 | 7/1991 | Magruder et al. . |
| 5,266,325 | 11/1993 | Kuzma et al. . |
| 5,300,079 | 4/1994 | Niezink et al. ........................ 604/116 |
| 5,306,251 | 4/1994 | Alexander . |
| 5,312,389 | 5/1994 | Theeuwes et al. ..................... 604/141 |
| 5,484,424 | 1/1996 | Cottenceau et al. ................... 604/282 |
| 5,637,097 | 6/1997 | Yoon ..................................... 604/178 |
| 5,674,240 | 10/1997 | Bonutti et al. ......................... 604/264 |

*Primary Examiner*—Wynn Wood Coggins
*Assistant Examiner*—Jennifer R. Sadula
*Attorney, Agent, or Firm*—Charles F. Costello, Jr.

[57] ABSTRACT

An implant dart has a head of solid material and a tubular body that contains one or more drug-delivery implant packages. The head has a blade at its front end with a chisel type point with a beveled end and a scooped face extending rearwardly to the body. The body is formed as a helical coil that makes the body tubular and permits the coil turns to be compressed and engage to make the body relatively rigid when the dart is injected into the subject. A passage from the head to the interior of the body provides fluid communication between the subject's body fluids and the implant packages. Wings extend from the head to guide entry of the dart into the subject and to lock it against withdrawal. The complete system comprises at least one dart and an injection mechanism which retains a subject's body part on a platen and feeds darts into the body part and generally parallel to the platen.

23 Claims, 3 Drawing Sheets

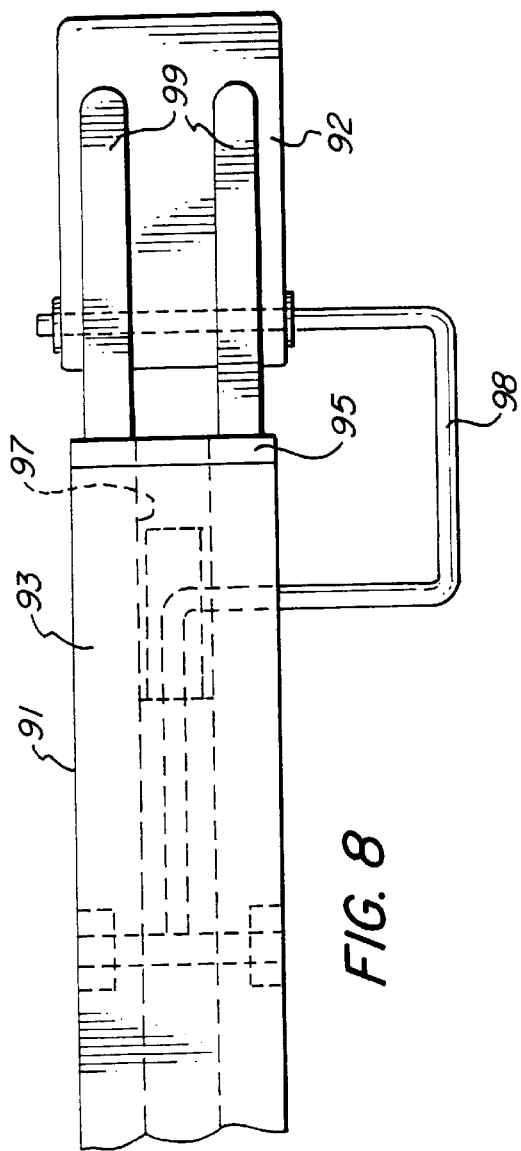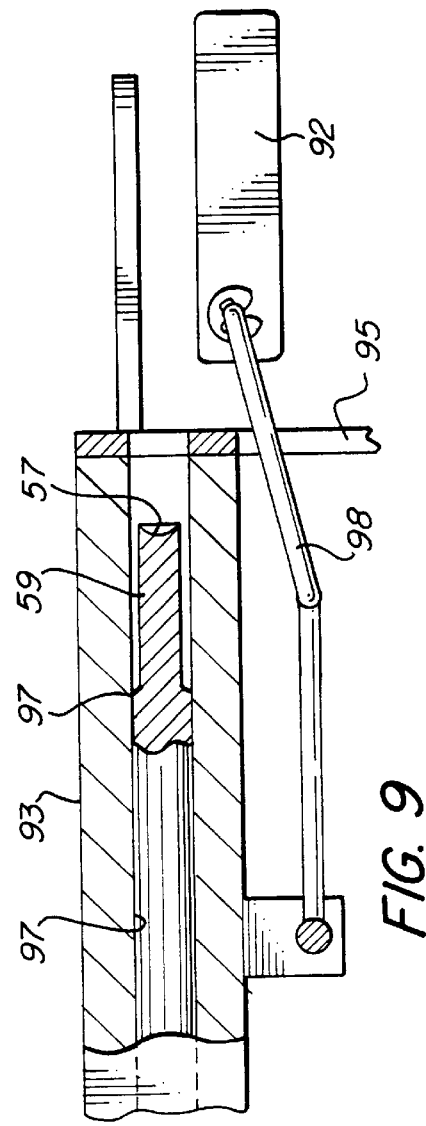

INJECTION DART SYSTEM

FIELD OF THE INVENTION

The present invention relates to a dart containing drug-delivery implants for insertion into the body of a subject, such as an animal, and a system for injecting the dart into the subject.

BACKGROUND OF THE INVENTION

Animals, particularly animals in the wild, have long been injected with tranquilizers and other drugs through the use of hypodermic darts propelled by means of a rifle or similar device. Such darts are constructed to lodge into the skin of the animal and to release their drug charge upon impact. The dart needs to be removed from the animal shortly after use, in order to avoid infection or other injury to the animal.

On the other hand, the need often exists to provide drug treatment to an animal over extended periods of time. Moreover, the drug may be of a type, such as a somatotropin, which would be broken down by the animal's digestive system if administered with its food supply. U.S. Pat. No. 5,266,325 granted to Kuzma et al. on Nov. 30, 1993 suggests that drugs which need to be administered over an extended period of time be provided in a sustained release drug-delivery implant which is injected subcutaneously into the living tissues of the subject. In accordance with Kuzma et al., the implant is introduced into the subject through a cannula of a large hypodermic needle/syringe-like instrument, which is removed from the subject's body immediately after injecting the implant. However, this method of introducing drugs is unsatisfactory for treating large groups of animals. For example, when treating cattle or pigs in the field, it would not be convenient to sterilize the hypodermic needle or to use a new needle for each animal. The danger therefore exists that a needle contaminated by one animal could infect an entire group.

Another shortcoming of utilizing implants is that they tend to shift in position. It therefore becomes very difficult, if not impossible, to detect whether a subject has or has not received an implant. Kuzma et al. suggests using a radioactive material within the implant to permit detection. However, in the field, this is not a satisfactory solution.

Broadly, it is an object of the present invention to provide a system for introducing sustained release implants into animals, which system avoids the shortcomings of known systems of this type. It is specifically contemplated that the system be capable of introducing implants to a large group of animals without the risk of spreading infection or disease among them.

It is another object of the invention that drug containing implants introduced into an animal be capable of remaining within the animal for extended periods of time, while their presence or the fact of their having been introduced is readily detectable, despite the depletion of the drug, and without the use of complex instruments.

It is yet another object of the present invention to inject implants containing one or more drugs into a subject animal without the need to invasively penetrate the bodies of multiple animals with a common instrument.

It is also an object of the present invention to provide a system and apparatus for introducing drug containing implants into the body of a subject, which system and apparatus are simple, convenient, and reliable in use, yet relatively inexpensive in construction.

In accordance with the present invention a dart containing drug-delivery implants is provided, which can be introduced and implanted readily in the subject's body at a given site, for example, subcutaneously in a pig's ear, without the use of an instrument which invades the subject's body.

In accordance with a preferred embodiment of the invention, the dart is of plastic material having a hollow cylindrical body and a solid head, generally of a cylindrical shape. The face of the dart head has a scoop shape and the exposed edge surface of the face has a fillet radius that starts at the top edge of the dart body and tapers downwardly and forward from the hollow body. This forms a relatively long narrow blade at the lower part of the head, the leading edge of which is formed with a sharp chisel point, to provide for penetration entry of the dart into the subject's body.

Flexible stabilizing wings are provided on either side of the dart head. The stabilizing wings sweep outwardly and backward toward the hollow cylindrical body and serve as a lock or barb to prevent the dart from being pulled out of the subject once it has entered the subject's body part.

The dart's hollow body is preferably a coil of material formed with a number of turns into a helix. This gives the body a degree of flexibility to permit the dart's body shape to change as it conforms to the darted site of the subject's body. The coil also makes the dart body compressible in a lengthwise direction, to provide rigidity as the dart is inserted under pressure into the subject. One or more implants, which may contain the same or different substances, are located within the hollow body. There is a passage through the dart head into the body to provide fluid communication between the subject's body fluids and the implant. An end cap is frictionally fitted into an opening at the rear of the body. The presence of the dart injected into the subject may be determined visually or by palpation of the subject's darted body part (e.g. the ear).

It is a feature of the invention that a dart which is pervious to body fluids is provided which carries implants containing one or more substances and that the dart is itself implanted directly into a subject, such as a pig.

A further feature of the invention is that a dart for carrying one or more implants is pervious to body fluids and includes a head with a blade having a sharp tip for penetrating the subject's body. The dart body contains one or more implants with substances to be released into the subject, so that the dart is readily injected into the subject and carries the implants with it.

It is yet another feature of the invention that a dart for carrying one or more implants into a subject is pervious to body fluids and has a body which is firm and rigid while being inserted into the subject, yet may expand in its lengthwise direction, to become flexible after insertion into the subject.

It is a further feature of the invention that the presence within a subject's body part of an injected dart containing drug-delivery implants may readily be determined visually or by palpation of the subject's body part.

BRIEF DESCRIPTION OF THE DRAWINGS

Other objects and advantages of the present invention will become more apparent with reference to the following specification in which:

FIG. 8 is a top view of a dart injection system or applicator in accordance with the present invention.

FIG. 9 is a left side view of the injection system of FIG. 8, with parts shown in section to illustrate further internal details of the system.

DETAILED DESCRIPTION OF THE INVENTION

Figure 1:
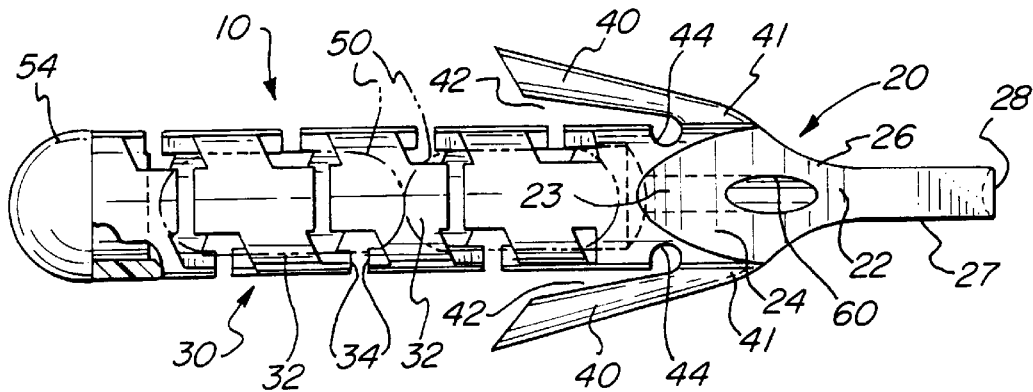
FIG. 1 is a top view of a preferred embodiment of a dart in accordance with the invention.

Referring to FIGS. 1–7, the dart 10 includes a solid head 20 generally having an overall cylindrical shape and a hollow tubular body 30. The dart is preferably of a biologically suitable plastic material such as a polycarbonate. The dart 10 is preferably made by injection molding and preferably in one piece. The dart head 20 is a solid piece with a top face 22 that curves downwardly in a scoop shape from a rear end 23 which is at the beginning of the front end of body 30. From the head rear end 23 there is a surface edge leading to concave radius 24 extending into a shallow, tapered surface 26. This terminates in an elongated projecting relatively narrow blade 27 having a sharpened cutting edge 28 with a downward bevel 29. The bottom surface of blade 27 is curved. A plow 25 creates a transition from the narrow blade 27 (see FIG. 1) to the cylindrical dart body 30 and serves a purpose to be described more fully below.

Figure 2:
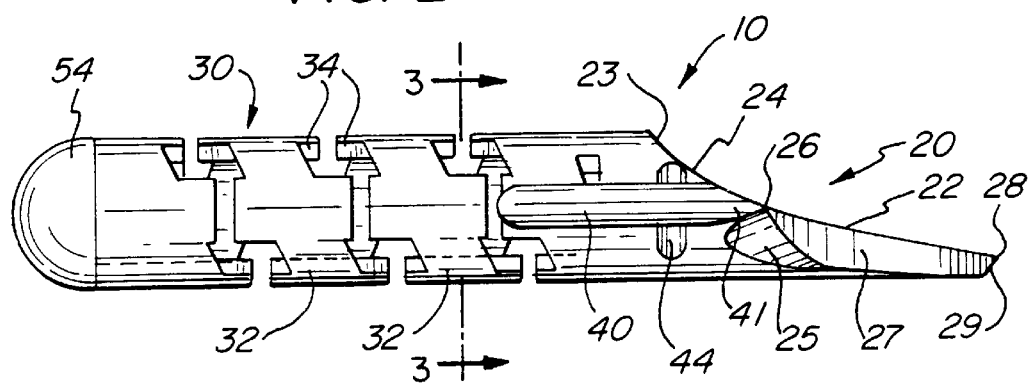
FIG. 2 is a side view of the dart shown in FIG. 1.
Figure 3:
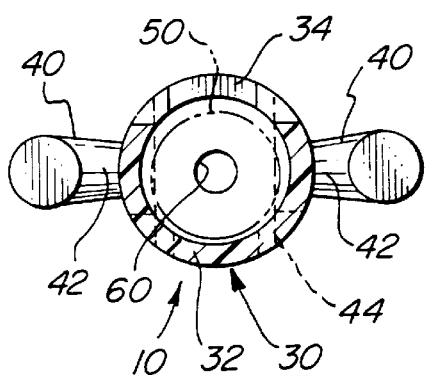
FIG. 3 is a sectional view taken along line 3—3 and looking in the direction of the arrows in the dart of FIG. 2.
Figure 4:
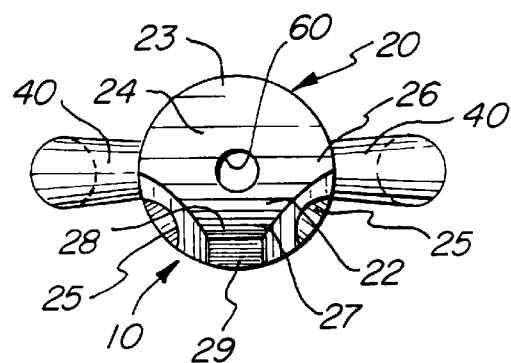
FIG. 4 is a front view of the dart in FIG. 2.

A pair of flexible wings 40 are formed on the outer surface of head 20 starting at the tapered surface 26. The wings 40 are swept back and overlie the front end of body 30. Wings 40 have a pointed leading edge 41 and lie in a horizontal plane, as illustrated in FIGS. 2–4, that is along the longitudinal center line of the dart body 30 and is parallel to a plane tangent to the bottom of the body as shown in FIG. 2. As seen in FIG. 1, each wing 40 has a relief slot 42 which is angled inwardly relative to the body that terminates in a generally circular end 44. The slots 42 permit the wings to flex inwardly. This prevents stress in the wings 40 when flexed upon insertion of the dart into the subject.

Figure 5:
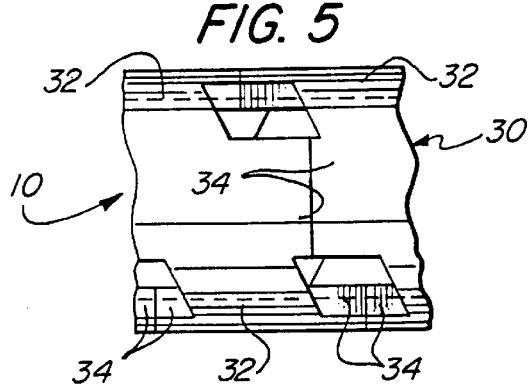
FIG. 5 is an enlarged fragmentary view of a portion of the dart of FIG. 1 showing the coils of the body compressed.

Body 30 is a coil of several turns 32 wound in a helix to form a hollow tube. The turns 32 of the coil have opposing stops 34 in the form of tabs. The tabs 34 have the same curved shape as the coil turns and are preferably spaced 90° apart around each side of each coil turn. The stops 34 of one coil turn face those of the next adjacent turn and the stops engage when the body 30 is compressed lengthwise during insertion into the subject. This is shown in FIG. 5.

One or more implant packages 50 (FIGS. 1 and 3) are located within the body 30 and contain any type of nutritional or medicant supplement of desired dosage or a combination thereof. The packages 50 are inserted into tubular body 30 through the open end of the body remote from head 20. An end cap 54 with a spherical radius is friction fitted into the end of the body 30 remote from the head.

A hole 60 provides a communicating passage through head 20 from its top face 22 to the inside of the body 30.

Therefore, when the dart is inserted into the subject, there is fluid communication between the body fluids of the subject to and with the implant packages 50 for release of their contents into the subject.

Figure 6:
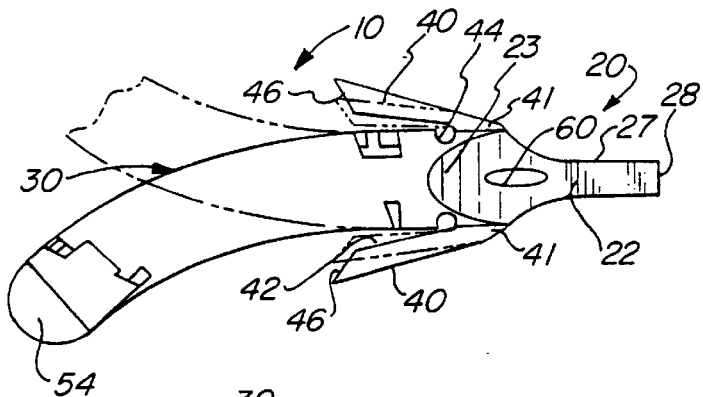
FIG. 6 is an overall schematic top view showing the flexing of the dart body and the compression of the dart wings.
Figure 7:
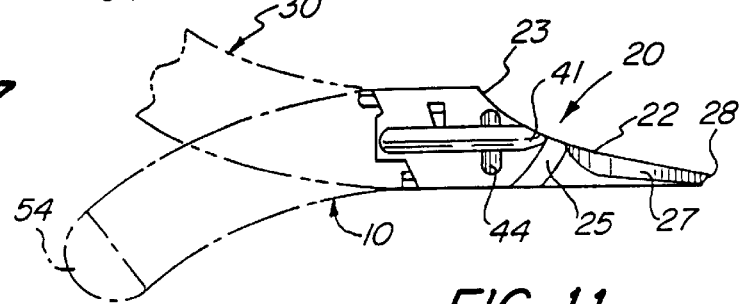
FIG. 7 is an overall schematic side view similar to FIG. 6.

FIGS. 6 and 7 show the flexibility of the body 30 in all directions. This permits the dart to conform to the subject's body, permitting normal movement of the darted body part and avoiding discomfort, irritations or rejection of the dart by the subject's body. In FIG. 6, the wings 40 are shown in the compressed state in dotted lines.

Figure 10:
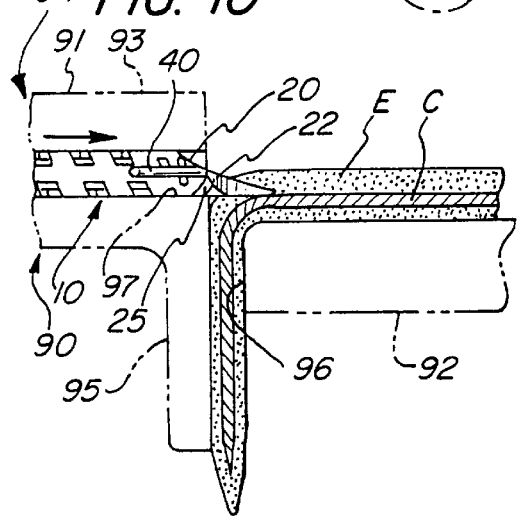
FIG. 10 is a fragmentary sectional view taken along line 9—9 in FIG. 8 after the ear of a subject has been captured and showing the initial insertion of a dart.
Figure 11:
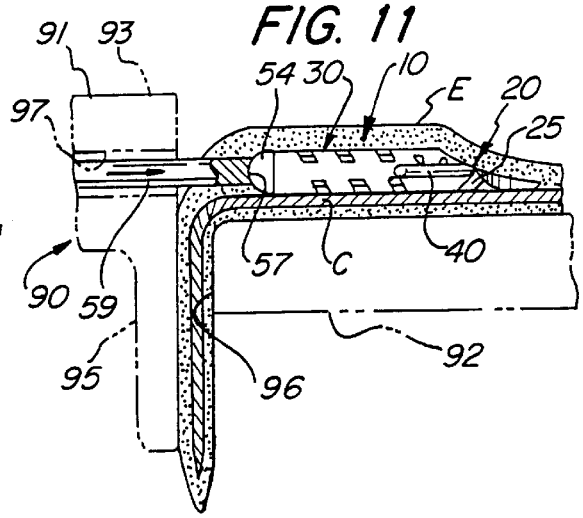
FIG. 11 is a view similar to FIG. 9 showing the dart completely inserted.

FIG. 8 is a plan view of a preferred embodiment of an implant dart applicator or insertion system 90 embodying the present invention, and FIG. 9 is a partially sectioned side view illustrating further details of the applicator system in use. System 90 broadly comprises a main body 91, which includes a chamber (not shown) adapted to receive a dart 10. At one end of body 91, a platen 92 is positioned and retained by means of a hinge member 98 so as to be pivotal relative to main body 91. (As used herein, the term platen refers to the engagement means for receiving and retaining a part of an animal's body, in accordance with the present invention). Main body 91, opposite platen 92, also includes a propulsion mechanism (not shown) is actualable to provide a propulsive force to the dart 10 inside main body 91, through a push bar 59, which accelerates the dart towards platen 92. The propulsion mechanism may be any type of conventional mechanism, but is preferably a spring operated device which may be loaded and then released, as by a trigger. As best seen in FIGS. 8–10, main body 91 includes a top part 93, which has a bore 97 in which dart 10 is accelerated towards platen 92. By means of hinge member 98, platen 92 may be conveniently pivoted relative to main body 91 so as to receive the ear (E) of the subject, into which the dart 10 is inserted. Ear (E) is then maintained flat against the top of platen 92 by means of arms 99, which engage it, and the ear is formed into a 90° bend in front of the exit (within the projected perimeter) of bore 97. In this position, the ear is held captive between platen 92 and leg 95.

The use of the dart 10 will now be explained. While description is made relative to inserting the dart into the ear of a pig, the dart can be used on other body parts or on other types of subjects, including cattle, sheep, goats or other livestock, or domestic or wild animals. In FIGS. 9 and 10 the flat platen 92 lies opposite the top part 93 with a downwardly extending leg 95. The pig's ear (E) has been captured between the platen 92 and leg 95 and is retained in a flat position on top of the platen and formed into a 90° bend.

In use, platen 92 is preferably offset sufficiently below the bore 97, which is parallel to the platen, to permit the ear cartilage C to be aligned generally with or below the bottom of bore 97 (i.e. outside the projected perimeter of the bore).

The dart is injected from bore 97 into the exposed top surface of the ear (E). With the blade curved bottom surface and wings 40 generally parallel to platen 92, the dart is caused to travel at a sufficient velocity to pierce the ear by propulsion mechanism 94. The dart's narrow, sharp chisel edge 28 cuts through the skin of the ear (E) with minimal resistance. Slight deflection occurs when the front of the dart penetrates the skin. As the dart travels further under the skin, the radius 24 and bottom plow 25 compensate to neutralize the downward forces. Resistance encountered at the top edge 23 causes the dart to lift, allowing it to travel across the upper surface of the cartilage. Radius 24 and wings 40 guide the dart across the cartilage, preventing blade 27 from penetrating therethrough. These details of these various mechanisms are explained in more detail below.

The shallow taper 26 at the inner end of the narrow blade 27 and the radius 24 create a drag that lifts the chisel edge 28. Owing to its shape, plow 25 further lifts and prevents the cutting edge 28 from penetrating cartilage. The bevel 29 continues deflecting the cartilage downwardly as the cutting edge 28 continues to cut through tissue during dart insertion. As a result, the dart slides along the surface of the cartilage as it advances.

The wings 40 provide orientation and rotational stability for the dart as it is being inserted. They also provide a locking feature once the dart is inserted into the subject. During insertion of the dart, the wings 40 are flexed inwardly (shown as dotted lines in FIG. 6). After insertion into the ear, the wings reflex to their outward position (as shown by the solid lines in FIG. 6). The wings stabilize the dart after entry into the subject. This maintains proper alignment of the dart and minimizes resistance at entry. A rear angle 46 on the wings 40 (FIG. 6) causes the wings to engage body tissue and spread out if the direction of the dart is reversed, thereby creating the locking feature.

During dart insertion the coils 32 of the body are compressed along the length of the body until the stops 34 engage (as shown in FIG. 3), owing to the high accelerating velocity imparted to the dart by the propulsion mechanism 94 (preferably 40–60 mph). This makes the dart collapse so as to be totally rigid at the point of entry into the subject. With the dart in the ear, there is communication between the subject's body fluids, e.g., blood, and the implant package 50 in body 30 through the head passage 60. This facilitates release of the implant contents into the subject's body.

After entry, upon any movement of the dart outwardly of the subject, complete removal of the dart is prevented by the locking wings. The coil turns of the body can separate somewhat as the ear moves so that the dart body is more conformable to the ear. This also provides additional communication between the implants 50 and the subject's body fluids.

The spherical radius shape of body end cap 54 provides positive location with the matching spherical radius 57 (FIG. 10) of a push bar 59 of the injection gun. This controls direction and prevents the end cap 54 from side slipping as a dart completes its travel into the ear.

Presence of the dart 10 in the subject can be detected visually or by palpation of the darted site. It also contemplated that the dart may include a small metal or magnetic element to permit its detection by a metal or magnetic detector, or the like. The dart may also include simple electronics to aid in detection and identification.

The dimensions of the dart 10 depend on a number of factors including, the dimensions of and the number of implants contained, the type of subject, depth of the dart insertion, insertion force needed to pierce the subject's skin etc. In the example of the pig's ear, shown in FIGS. 8 and 9 the dart 10 has an overall length of about 45 mm and an outside diameter of about 7 mm.

Although preferred forms of the invention have been disclosed for illustrative purposes, those skilled in the art will appreciate that many additions, modifications, and substitutions are possible without departing from the scope and spirit of the invention as defined by the accompanying claims. For example, although not as desirable, the dart 10 need not be accelerated into the subject's body part by means of a propulsion device. Instead, it would be possible to make a small incision in the subject's body part and to inject the dart into the body part at low speed, as by operating the push bar 59 manually.

We claim:

1. An implant dart for insertion into an animal body, said implant dart comprising:

a forward head having a first means for penetrating into body tissue so as to permit the entire dart to enter and lodge totally within the body and a second means for non-removably implanting said entair dart within said body, a tubular body oriented behind said head, said tubular body having a compartment for holding at least one drug-delivery implant container; said compartment in said tubular body being in fluid communication with said head by a passage defined between said head and said tubular body to permit entry of fluids within the animal body into said compartment;

said forward head and said tubular body being formed from material biologically compatible with said animal body.

2. An implant dart as in claim 1 wherein said head comprises a front end thereof and said tubular body comprises a rear end thereof, said front end being constructed to be sufficiently sharp to pierce body tissue.

3. An implant dart as in claim 2 wherein said head has an outer surface, is of curved shape and includes a face with a scooped shape.

4. An implant dart as in claim 3 wherein the front end of said head is an elongated blade having a forward end, said forward end defining an upper cutting edge and an inwardly and downwardly oriented bevel defined below said cutting edge.

5. An implant dart as in claim 4, wherein said head has a concave radius defined between a rear end portion of said head and a rear end portion of said blade.

6. An implant dart as in claim 2 wherein said tubular body is flexible.

7. An implant dart as in claim 6 wherein the tubular body is formed of at least one turn of a coil of material.

8. An implant dart as in claim 7, wherein said at least one turn is of a helical shape.

9. An implant dart as in claim 6 further comprising an opening at the end of the tubular body remote from the head to permit insertion of an implant into said tubular body.

10. An implant dart as in claim 1 further comprising a plug for sealing the rear end of said tubular body remote from said head.

11. An implant dart for insertion into an animal body, said implant dart comprising:

a head having means for penetrating into body tissue so as to permit the entire dart to enter the body;

a tubular body having a compartment for holding at least one drug-delivery implant container; said tubular body being pervious to fluids within the animal body so as to permit entry of said fluids within the animal body into said compartment;

said head comprising a front end of said dart and said tubular body comprising a rear end of said dart, said front end of said head being constructed to be sufficiently sharp to pierce body tissue;

said tubular body being flexible;

said tubular body being formed of at least one turn of a coil of material, said at least one turn being of a helical shape; and the coil having a plurality of turns and stops between the turns of the coil that engage to limit compressive force along the length of the tubular body.

12. An implant dart for insertion into an animal body, said implant dart comprising:

a forward head having means for penetrating into body tissue so as to permit the entire dart to enter the body;

a tubular body oriented behind said head, said tubular body having a compartment for holding at least one drug-delivery container; said compartment in said tubular body being in fluid communication with said head by a passage defined between said head and said tubular body to permit entry of fluids within the animal body into said compartment; and at least one stabilizing wing extending from said head back towards said tubular body.

13. An implant dart as in claim 12 wherein said at least one wing overlies at least a part of said tubular body.

14. An implant dart as in claim 12 wherein there are a pair of substantially coplanar stabilizing wings on opposing sides of said head.

15. An implant dart as in claim 14 wherein said wings are located on a plane which passes through the longitudinal axis of the tubular body.

16. An implant dart as in claim 14 wherein said stabilizing wings are formed in a delta shape.

17. An implant dart as in claim 14 wherein each said wing has a slot starting at a rear edge thereof and being generally parallel to the longitudinal axis of the tubular body to permit flexing of a wing inwardly toward the tubular body.

18. An implant dart for insertion into an animal body, said implant dart being formed from material biologically compatible with said animal body and adapted to be non-removably implanted in said animal body, said implant dart comprising at least two separate components including:

a head portion comprising a forward end of said dart, said head portion having a first means for penetrating the animal body to permit said entire dart to enter and lodge totally within the animal body and a second means for non-removably implanting said entair dart within said body, a tubular body being oriented behind said forward head portion and comprising a rear end of said dart, said tubular body being adapted for holding at least one drug-delivery implant container therein;

said forward head portion defining at least one opening therein in fluid communication with said tubular body for releasing substances in said drug-delivery implant container from said dart;

said forward head and said tubular body being formed from material biologically compatible with said animal body.

19. An implant dart for insertion into a subject comprising:

a head having a front and rear end and an elongated blade at its front end;

a flexible tubular body at the rear end of said head formed of a coil of material;

at least one implant within said tubular body; and said head having a passage therethrough communicating with the interior of said tubular body.

20. An implant dart for insertion into an animal body, said implant dart comprising:

a head comprising a front end of said dart and having a first means for penetrating into body tissue so as to permit the entire dart to enter and lodge totally within the body and a second means for non-removably implanting said entair dart within said body, a flexible tubular body comprising a rear end of said dart and having a compartment for holding at least one drug-delivery implant container;

a passage through said head to the interior of said tubular body for providing access into said compartment by fluids within the animal body;

an opening at the end of the tubular body remote from the head to permit insertion of an implant into said tubular body;

said forward head and said tubular body being formed from material biologically compatible with said animal body.

21. A method for implanting a sustained release composition into an animal body, said method being performed with an implant dart including a head having means for penetrating into body tissue so as to permit the entire dart to enter the body, a tubular body having a compartment for holding a drug-delivery implant container, a passage between said head and said compartment to permit entry of fluids within the animal body into said compartment, said method comprising the steps of:

introducing into said compartment a drug-delivery implant containing said sustained release composition; and inserting said implant dart into the interior of a part of the animal body so that the dart is entirely within the body part and said fluids within the animal body are in fluid communication with said drug-delivery implant in said compartment.

22. The method of claim 21 wherein the body part into which said implant dart is inserted is an animal's ear and said inserting step comprises:

retaining the ear so that a target portion thereof extends along a path of travel of said dart while an adjacent portion extends laterally of said path, whereby an angular bend in the ear is exposed to said dart; and advancing said dart towards the ear so that it enters the ear at the angular bend and advances along the target portion.

23. The method of claim 21 wherein the body part into which said implant dart is inserted is an ear containing cartilage, said method being performed with the aid of an applicator including a housing having an elongated bore dimensioned to receive the dart and terminating in an forward opening in said housing, said forward opening being defined by a perimeter of said bore, and engagement means for receiving and retaining the ear, said inserting step comprising:

positioning said engagement means relative to said housing so that a target portion of the ear is positioned generally parallel to and in front of said forward opening with the cartilage thereof outside the perimeter of the bore, while an adjacent area of the ear extends laterally of said forward opening so as to expose a bend in the ear at said forward opening; and placing a dart in said bore means at a distance rearward of said forward opening and accelerating said dart towards and out of said forward opening.

* * * * *